United States Patent [19]

Fleming

[11] Patent Number: Plant 7,427

[45] Date of Patent: Jan. 22, 1991

[54] KALANCHOE PLANT NAMED GREMLIN

[75] Inventor: Margaret M. Fleming, Soquel, Calif.

[73] Assignee: The Plant Company, Soquel, Calif.

[21] Appl. No.: 422,088

[22] Filed: Oct. 16, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Kalanchoe plant named Gremlin particularly characterized by its red flower color; flower diameter of 13 to 15 mm at maturity; flowering response of from 10 weeks in summer to 12 weeks in winter after start of short days; good keeping quality of flowers and foliage; branches freely with or without pinching; compact plant habit with short internodes and medium sized foliage, and recommended for flowering in 10 cm pots and smaller.

2 Drawing Sheets

The present invention relates to a new and distinctive cultivar of Kalanchoe plant, botanically known as *Kalanchoe blossfeldiana* Poelln., and referred to by the cultivar name Gremlin.

Gremlin, identified at 604-001, is a product of a planned breeding program which had the objective of creating new Kalanchoe cultivars for year-round commercial production, with earlier flowering response, good branching yet compact flowering plants, and with good flower and foliage keeping quality.

Gremlin was originated by the inventor Margaret M. Fleming from a controlled selfing of the parent plant, an unnamed seedling identified as 409-021, now referred to by the varietal designation Small Wonder, disclosed in a pending plant patent application of the present inventor, in Half Moon Bay, Calif., in 1984.

Gremlin was discovered and selected by the inventor as one flowering plant within the progeny of the stated selfing in February, 1986 in a controlled environment in Soquel, Calif.

The first act of asexual reproduction of Gremlin was accomplished when vegetative cuttings were taken by the inventor from the initial selection in July of 1986 in a controlled environment in Soquel, Calif.

Horticultural examination of controlled flowerings of successive plantings has shown that the unique combination of characteristics as herein disclosed for Gremlin are firmly fixed and are retained through successive generations of asexual reproduction. Gremlin has not been observed under all possible environmental conditions. The phenotype may vary significantly with variations in environment such as temperature, light intensity and daylength.

The following observations, measurements and comparisons describe plants grown in Soquel, Calif., under greenhouse conditions which approximate those generally used in commercial greenhouse practice.

The following traits have been repeatedly observed and are determined to be basic characteristics of Gremlin, which, in combination, distinguish this Kalanchoe as a new and distinct cultivar:

1. Red flower color.
2. Flower diameter of 13 to 15 mm at maturity.
3. Flowering response of from 10 weeks in summer to 12 weeks in winter after start of short days.
4. Good keeping quality of flowers and foliage.

5. Branches freely with or without pinching.
6. Compact plant habit with short internodes and medium sized foliage.
7. Recommended for flowering in 10 cm pots and smaller.

The accompanying photographic drawings show typical inflorescence and leaf characteristics of Gremlin, with colors being as nearly true as possible with illustrations of this type. Sheet 1 is a color photograph of Gremlin grown as a non-pinched flowering Kalanchoe in a 10 cm pot. Sheet 2 is a black and white photograph showing the leaves of Gremlin at three stages of development (mature, intermediate and immature).

Of the commercial cultivars known to the inventor, the most similar in comparison to Gremlin is the cultivar identified as Tropicana, disclosed in U.S. Plant Pat. No. 5,961. Similar traits are flower size, free branching, compact plant habit with short internodes and medium sized foliage, and suitability for production in small pots. The flower color of Gremlin is clear red, while the flower color of Tropicana is more orange-red. In addition, the flowering response of Gremlin is two to three weeks faster than the response of Tropicana.

Gremlin can also be compared with its parent Small Wonder, and the male and female parents Regulus and Eternity, respectively, of Small Wonder. With regard to Small Wonder, Gremlin is substantially more compact, has orange-red flower color compared with the more apricot-orange (with red highlights) color of Small Wonder, and its larger leaves are slightly darker green in color.

In comparison with Eternity, Gremlin is a faster grower, has smaller and less fleshy or succulent foliage which is a lighter green in color, has a blooming response which is 1–2 weeks earlier, and flowers which are smaller in diameter and red-orange in color, as opposed to the salmon pink flower color of Eternity. A further important distinction is that Gremlin to date has not been observed to fade under high temperature or low light conditions. Both cultivars are commonly characterized by the important commercial characteristic of extra long keeping qualities.

In comparison to Regulus, Gremlin is more compact, its foliage is somewhat larger but not as fleshy, and its florets are smaller and a clear bright red-orange in color, as opposed to the less bright and more orange flower color of Regulus. In addition, Gremlin has not inherited certain weaknesses in Regulus, including early degradation of the lower foliage, a propensity for tip die-back, and an over sensitivity of its roots to salt buildup and overwatering.

In the following description color references are made to The Royal Horticultural Society Colour Chart. The color values were determined on plant material grown as a non-pinched pot plant in a 10 cm pot in Soquel, Calif., on Aug. 9, 1988.

Classification:

*Botanical.*—*Kalanchoe blossfeldiana* Poelln. cv. Gremlin.

*Commercial.*—Flowering pot Kalanchoe.

Parentage: A controlled selfing of an unnamed seedling, identified as 409-021.

Propagation:

(A) *Type cutting.*—Short tip cutting, with stems up to 2 cm.

(B) *Time to root.*—10 days at 21° C. in summer, 14 days at 21° C. in winter.

(C) *Rooting habit.*—Many very fine roots, fibrous.

Plant description:

(A) *Form.*—Short, compact, upright growth. Growing and scheduling practices can produce a small plant in a 10 cm and smaller pot.

(B) *Habit of growth.*—Rate of growth slow for this type of plant. Generally, shoots are formed at every node; internode length of natural vegetative plant, 10–20 cm.

(C) *Height.*—Short, 10–15 cm. above a 10 cm. pot, with 0–1 application of 3500 ppm B-9 SP linear growth regulator.

(D) *Foliage description.*—Leaves simple, opposite, slightly lobed. 1. Size: Average full grown leaf in a 10 cm flowering pot is 120 mm long×75 mm wide. 2. Shape: Ovate to elliptic, apex obtuse to slightly pointed, base attenuate. 3. Texture: Glabrous, coriaceous, succulent. 4. Margin: Sinuate to crenate. 5. Color: Mature foliage: Upper surface 147A. Under surface 147B. Under certain conditions tips and margins of mature foliage on both upper and under surface are slightly streaked with 183A to 183C. 6. Durability: Excellent; no degradation observed even on the lower foliage of plants retained for months beyond normal expectancy.

Flowering description:

(A) *Flowering habit.*—Inflorescence of each shoot is formed by dichotomous branching, starting with opening of terminal of main axis, followed by terminal flowers of the side branches, continuing with subsequent development of branches in the inflorescence. Opening of new buds (10–13 mm. in length) will continue for two months or more. Individual flowers last two weeks or more after opening.

(B) *Flowering response.*—Flowering time under controlled daylength after start of short days is 10 weeks in summer to 12 weeks in winter.

(C) *Flowers borne.*—Compound dichasial cymes; peduncle length is 4–9 cm. in length and 3–6 mm. in diameter, depending on growing conditions and application of growth regulator; pedicels 4–6 mm. in length and less than 1 mm. in diameter.

(D) *Quantity of flowers.*—Very floriferous, on both the main axis and side laterals; typical floret count of 80–100 per major inflorescence and 400–500 total per plant in a 10 cm. pot grown in accordance with commercial culture practices; 4 to 6 side laterals in a 10 cm pot.

(E) *Petals.*—1. Shape: Pointed to almost round. 2. Color: Upper surface: 40A to 40B. Under surface: Closest to 38C, slightly streaked with 40B. 3. Number of petals: 4, united in corolla. 4. Flower diameter: 13 to 15 mm at maturity.

(F) *Reproductive organs.*—1. Stamens: 8 in number. a. Anther shape: Flat, elliptical, color yellow. b. Filament color: Light green. c. Pollen color: Yellow. 2. Pistils a. Stigma shape: Flat, crystalline, color greenish white. b. Style color: Light green. c. Ovaries: 4-celled, color light green.

(G) *Keeping quality.*—Excellent; flowers last two weeks or more, with the plant being in flower two months or more.

Disease resistance: Gremlin is resistant or immune to the foliar disease Powdery Mildew and no occurrences of chlorosis, necrotic spot, tip die-back, root rot, or stem rot have been observed. Gremlin is also resistant or immune to the flower disease Botrytis, and no fading or color breaking has been observed.

Fragrance: None perceived in flowers or foliage.

I claim:

1. A new and distinct plant of Kalanchoe named Gremlin, as described and illustrated.

* * * * *

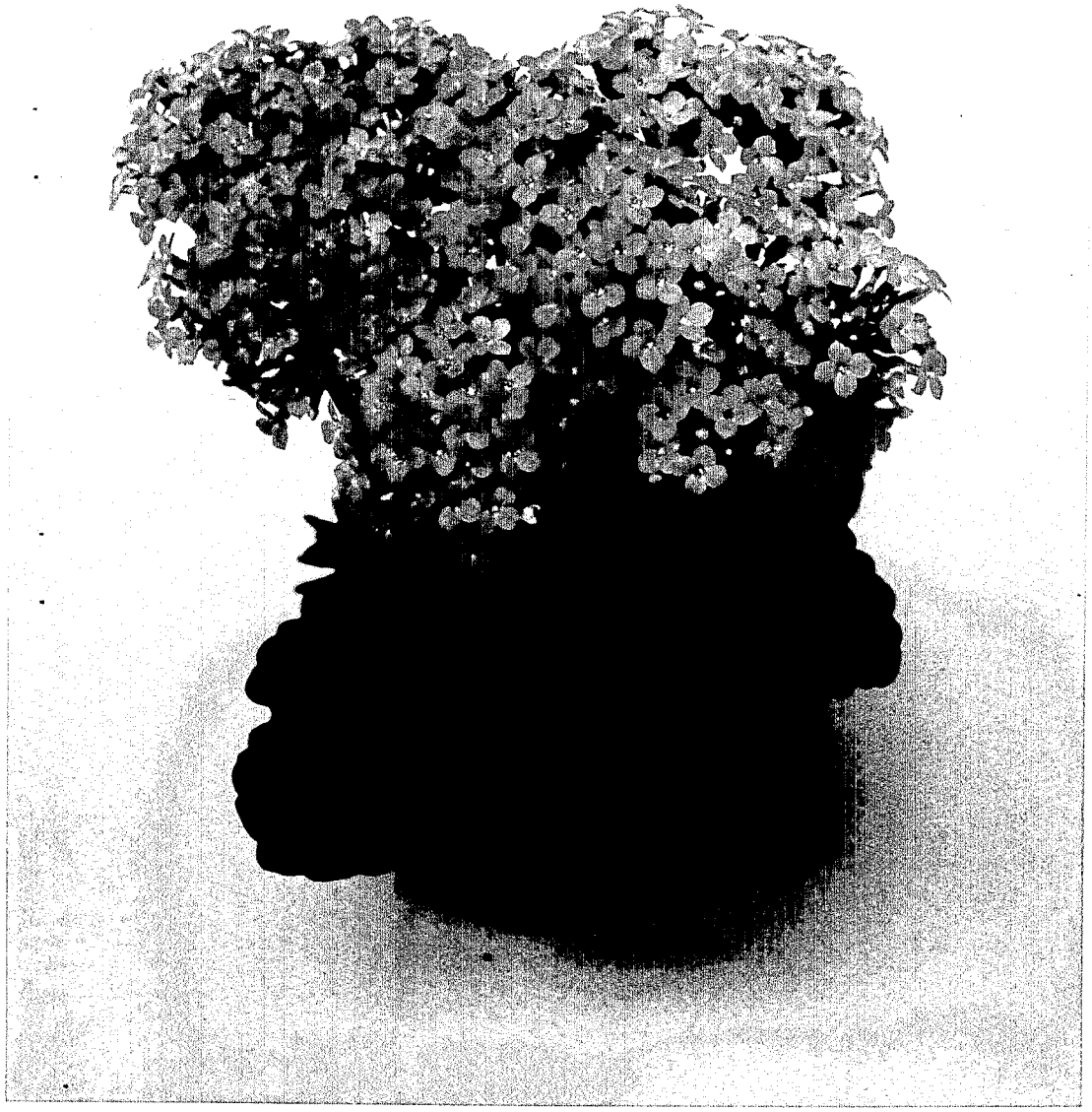

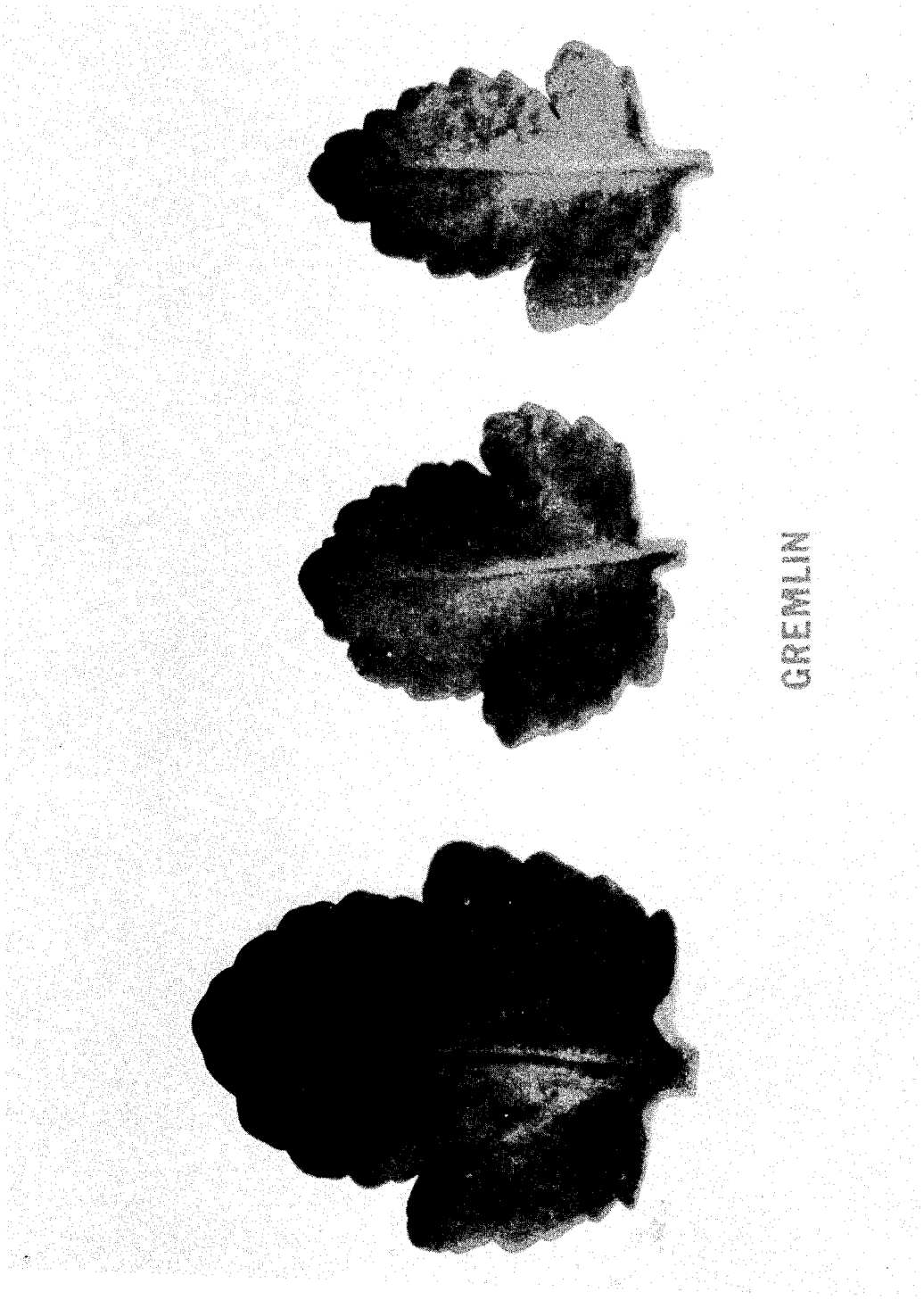
GREMLIN